(12) United States Patent
Sabetsky

(10) Patent No.: US 7,544,656 B2
(45) Date of Patent: Jun. 9, 2009

(54) LONG ACTING INJECTABLE INSULIN COMPOSITION AND METHODS OF MAKING AND USING THEREOF

(75) Inventor: Vladimir Sabetsky, Saint-Petersburg (RU)

(73) Assignee: The Technology Development Company, Ltd. (LU)

( * ) Notice: Subject to any disclaimer, the term of this patent is extended or adjusted under 35 U.S.C. 154(b) by 613 days.

(21) Appl. No.: 10/792,383

(22) Filed: Mar. 4, 2004

(65) Prior Publication Data

US 2004/0234616 A1    Nov. 25, 2004

Related U.S. Application Data

(60) Provisional application No. 60/495,097, filed on Aug. 15, 2003, provisional application No. 60/469,017, filed on May 9, 2003, provisional application No. 60/467,601, filed on May 5, 2003, provisional application No. 60/451,245, filed on Mar. 4, 2003.

(51) Int. Cl.
*A61K 38/28* (2006.01)

(52) U.S. Cl. ............... 514/3; 424/400; 436/529; 514/59; 524/54

(58) Field of Classification Search ............ 514/3, 514/59; 424/400; 436/529; 524/54
See application file for complete search history.

(56) References Cited

U.S. PATENT DOCUMENTS

| | | | |
|---|---|---|---|
| 4,713,249 | A | 12/1987 | Schroder |
| 4,963,526 | A | 10/1990 | Ecanow |
| 6,264,943 | B1 | 7/2001 | Cherksey |
| 6,303,148 | B1 | 10/2001 | Hennink et al. |
| 6,395,302 | B1 | 5/2002 | Hennink et al. |
| 6,482,413 | B1 | 11/2002 | Chalasani et al. |
| RE37,950 | E | 12/2002 | Dunn et al. |
| 2002/0054914 | A1 | 5/2002 | Morcol et al. |
| 2004/0048782 | A1 | 3/2004 | Bryson |

FOREIGN PATENT DOCUMENTS

| EP | 1 371 364 A | 12/2003 |
|---|---|---|
| WO | WO 87/02704 A | 5/1987 |
| WO | WO 99/02107 A | 1/1999 |
| WO | WO 02/28374 A1 | 4/2002 |
| WO | WO 02/39985 A | 5/2002 |

OTHER PUBLICATIONS

Eliaz R., Szoka F., Gene Therapy 9 (2002): 1230-1237.
Blain J.F., Maghni K., Pelletier S. and Sirois P. Inflamm. Res. 48 (1999): 386-392.
Crystallized carbohydrate spheres as a slow release matrix for biologically active substances, Ulf Schroder, Biomaterials 1984, vol. 5 March.
Crytallized Carbohydrate Spheres for Slow Release and Targeting, Ulf Schroder, Methods in Enzymology, vol. 12.
Surfactant-Free Preparation of Biodegradable Hydrogel Microspheres for Protein Release, Yasuhiko Tabata, et al., Journal of Bioactive and Compatible Polymers, vol. 14-Sep. 1999.
Partitioning in Aqueous Two-Phase Systems. A comprehensive bioliography in three parts: (1956-1984; 1985-1990; 1991-present) Part III: 1991-present Part II: 1985-1990.
Local and distant transfection of mdx muscle fibers with dystrophin and LacZ genes delivered in vivo by synthetic microspheres, A. Baranov, et al., Gene Therapy 6 (1999), 1406-1414.
Regulated insulin release from biodegradable dextran hydrogels containing poly(ethylene glycol), Kazuteru Moriyama, et al., Journal of Controlled Release 42 (1996) 237-248.
Lantus Prescribing Information—Aventis Pharmaceuticals (http://www.aventis-us.com/PIs/Iantus_TXT.html visited Feb. 23, 2004.
Sephadex-based cell-affinity adsorbents: preparation and performance, Geert Besselink, et al, Biotechnol., Appl. Biochem. 35 (2002), 55-60.
Formation of dextran hydrogels by crystallization, R.J.H. Stenekes, et al., Biomaterials 22 (2001) 1891-0898.
Enhanced Loading and Activity Retention of Proteins in Hydrogel Delivery Systems, S.H. Gehrke, et al, Proceed. Intern. Symp. Control. Rel. Bioact. Mater., 22 (1995), Controlled Release Society, Inc., p. 145-146.
Amidon GL, Lee HJ, Absorption of Peptide and Peptidomimetic Drugs, Ann. Rev. Pharamcol. Toxicol 1994; 34:321-41.
Abstract, Pharamcological Management of Type 2 Diabetes Mellitus: rationale for rational use of insulin., Mayo Clin Proc. Apr. 2003; 78(4): 459-67, Chan JL, Abrahamson MJ, May Clin Proc. Apr. 2003;78(4):411-3.
Soon-Shiong, "Encapsulated islet cell therapy for the treatment of diabetes: Intraperitoneal injection of islets," *Journal of Controlled Release*, May 1, 1996, pp. 399-407, vol. 39, No. 2, Elsevier Science Publishers B.V., Amsterdam, NL.
Crytallized Carbohydrate Spheres for Slow Release and Targeting, Ulf Schroder, Methods in Enzymology, vol. 112, pp. 116-128 (1985).
US 5,849,884, 12/1998, Woiszwillo et al. (withdrawn)

*Primary Examiner*—David Lukton
(74) *Attorney, Agent, or Firm*—Alston & Bird LLP

(57) ABSTRACT

A method of lowering blood glucose in a mammal includes injecting a therapeutically effective amount of crystallized dextran microparticles and insulin to the mammal to lower blood glucose of the mammal. The composition may be a one phase or a structured multi-phase composition for controlled release of insulin over an extended period of time.

10 Claims, 9 Drawing Sheets

US 7,544,656 B2

LONG ACTING INJECTABLE INSULIN COMPOSITION AND METHODS OF MAKING AND USING THEREOF

FIELD OF THE INVENTION

This application claims benefit of the following U.S. Provisional Applications Ser. Nos. 60/451,245, filed Mar. 4, 2003; 60/467,601 filed May 5, 2003; 60/469,017 filed May 9, 2003; and 60/495,097 filed Aug. 15, 2003, the disclosures of which are incorporated by reference herein in their entirety.

The present invention relates generally to insulin compositions and specifically to an injectable insulin composition containing insulin and crystallized dextran microparticles.

BACKGROUND OF THE INVENTION

Dextrans are high molecular weight polysaccharides synthesized by some micro organisms or by biochemical methods. Dextran with average molecular weight of about 75 kDa has a colloid osmotic pressure similar to blood plasma, so its aqueous solutions are used clinically as plasma expanders. Cross-linked dextrans in the form of beads are the basis for "Sephadex"® that is used in the GPC of proteins and for "Cytodex"® developed by Pharmacia to fulfill the special requirements of a micro-carrier cell culture. For example, U.S. Pat. Nos. 6,395,302 and 6,303,148 (Hennink et al.) disclose attaching various biomaterials to cross-linked dextran particles. However, beads based on cross-linked dextran generally cannot be used for implant manufacturing owing to their potential toxicity due to the application of cross-linking agents (Blain J. F., Maghni K., Pelletier S. and Sirois P. Inflamm. Res. 48 (1999): 386-392).

U.S. Pat. No. 4,713,249 (Schroder) describes a method of producing a depot matrix for biologically active substances. According to this patent, the depot matrix allegedly consists of carbohydrate microparticles, stabilized by crystallization, which implies using non-covalent bonds. The following process for producing the alleged crystallized carbohydrate microparticles is described by Schroder. A solution of a polymeric carbohydrate and a biologically-active substance is formed in one or more hydrophilic solvents. Then the mixture of the carbohydrate and the biologically active substance is emulsified in a liquid hydrophobic medium to form spherical droplets. The emulsion is then introduced into a crystallizing medium comprising acetone, ethanol or methanol to form spheres having a non-covalently cross-linked crystalline polymeric carbohydrate matrix, said matrix incorporating 0.001-50% by weight of the biologically-active substance. Thus, the biologically active substance is provided into the solution prior to crystallizing the spheres. Schroder does not describe the microstructure of the microparticles made by the multi-step method. Schroder's multi-step method is complex and uses organic solvents that are potentially toxic to cells and need to be removed.

BRIEF SUMMARY OF THE INVENTION

A method of lowering blood glucose in a mammal includes injecting a therapeutically effective amount of crystallized dextran microparticles and insulin to the mammal to lower blood glucose of the mammal. The composition may be a one phase or a structured multi-phase composition for controlled release of insulin over an extended period of time.

DETAILED DESCRIPTION OF THE PREFERRED EMBODIMENTS

The present inventor has discovered that a composition of crystallized dextran microparticles and insulin injected into mammals unexpectedly extended the duration of efficacy of the insulin compared to injections of the same dose of the same insulin alone. The composition may be a one phase composition or a multi-phase composition which forms a structured implant in a mammal.

The first section below describes the crystallized dextran microparticles, the second section describes formation of the structured implant from a multiphase composition, and the following sections describe specific examples of injection of the composition into mammals and methods of making the injectable composition.

A. Crystallized Dextran Microparticles

The present inventor has experimentally found that crystallized dextran microparticles with an average diameter ranging from 0.5 to 3.5 microns were spontaneously formed in concentrated aqueous solutions of dextrans (40-65% W/W)

with molecular weights ranging from 1.0 to 200.0 kDa, at temperature ranging from 20-90° C. If it is desired to form the microparticles at room temperature, then 2 to 18 kDa dextran solutions may be used. Of course, the microparticles may also be formed from 2 to 18 kDa solutions at temperatures above room temperature, if desired. The microparticles may be spontaneously formed from higher molecular weight dextran solutions, such as 20 to 75 kDa solutions, at higher temperatures above room temperature, such as about 40 to about 70° C. The microparticles may have any suitable shape such as a regular or an irregular shape, but are preferably spherical in shape, and are preferably 10 microns in diameter or less, such as 0.5 to 5 microns.

Figure 1:
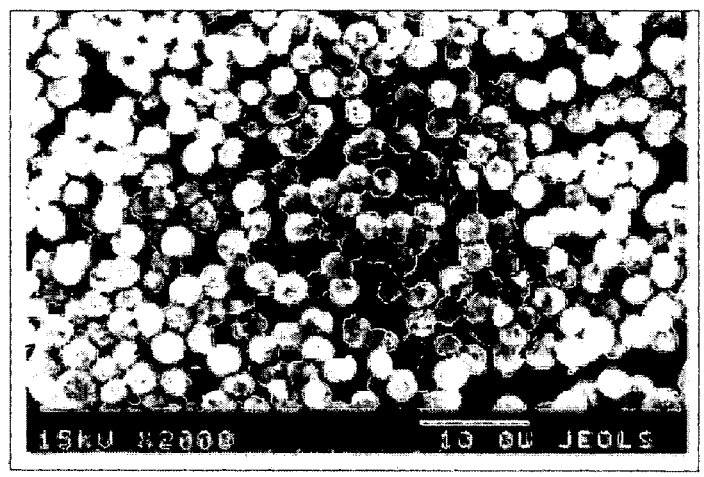
FIG. 1 is a photograph of crystallized dextran microparticles spontaneously formed in 55.0% (W/W) aqueous solution of dextran with MW 70.0 kDa.
Figure 2A:
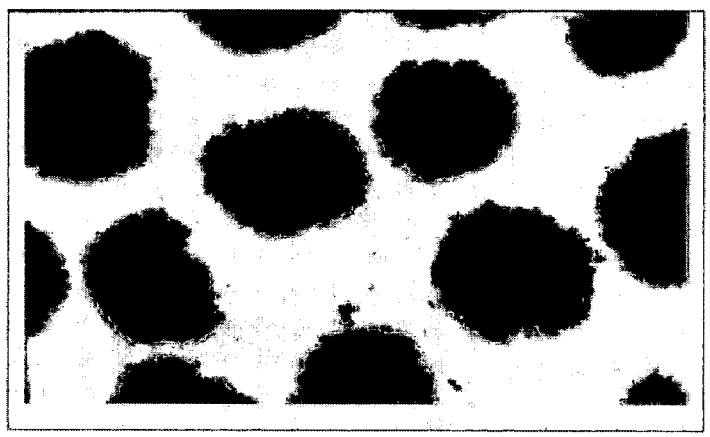
FIG. 2A is a photograph of a cross-section of crystallized dextran microparticles shown in FIG. 1.
Figure 2B:
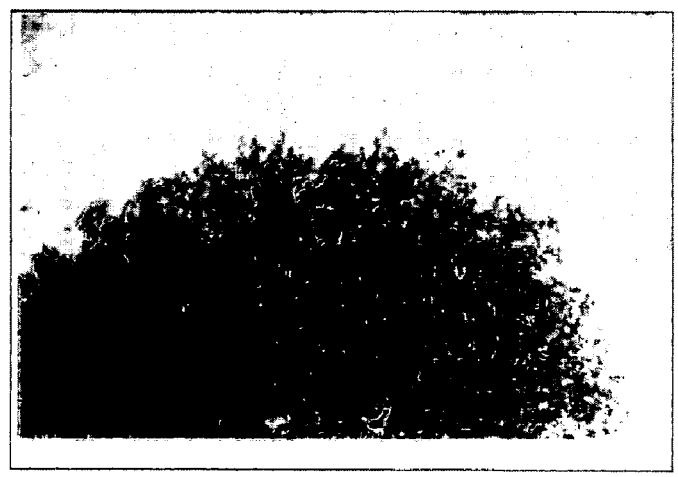
FIG. 2B is a photograph of a cross-section of a microparticle shown in FIG. 2A. Microporous structure of the microparticle can be seen.

Transmission Electron Microscopy revealed the microporous structure of the crystallized dextran microparticles (see FIGS. 2A, 2B). Preferably, the microparticle porosity is at least 10 percent by volume, such as about 10 to about 50 percent, more preferably about 20 to about 40 percent. Thus, the structure comprises microporous microparticles with areas of macroporosity located between the particles.

Figure 3:
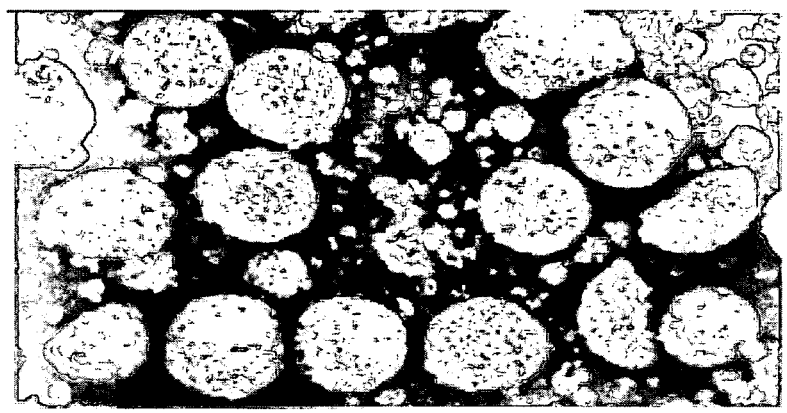
FIG. 3 is a photograph of aggregates of crystallized dextran microparticles.

Spray drying of aqueous suspensions of the crystallized dextran microparticles has shown the possibility to produce substantially spherical aggregates of crystallized dextran microparticles with a diameter ranging from 10.0 to 150.0 microns (see FIG. 3).

A non limiting example of a method of forming the dextran microparticles is as follows. 50.0 g of dextran T40 (40 kDa molecular weight) from Amersham Biosciences is added to 50.0 g of sterile distilled water in a 500 ml lab beaker to obtain 50% w/w solution under laminar flow. The mixture is stirred at 60° C. (water bath) on a magnetic stirrer at 50 rpm until the dextran is completely dissolved and a clear solution is obtained. The solution can be vacuumed to remove all air inclusions. The clear solution is placed in lab oven at 60° C. under a Tyvek® lid. 3.5 hours later, a turbid viscous suspension is developed as a result of formation of crystallized dextran microparticles.

To eliminate non-crystallized dextran, the microparticles are washed by centrifugation, for example 3,000 g, 30 min, with 3×250 ml of distilled sterile water, or by filtration of diluted suspension of microparticles, for example one part microparticles and 10 parts water (3×250 ml of distilled sterile water through sterilization filter). The centrifugation/washing is done under laminar flow. The microparticles are placed in 500 ml lab beaker under a Tyvek® lid and dried at 60° C. in lab oven for 8 hours to reach a moisture level of about 5%. The resulting dry powder consists of particles with a mean diameter of about 2 microns.

The crystallized microparticles preferably are comprised of dextran molecules (i.e., polymer molecules) that are held together by a plurality of hydrogen bonds, Van Der Waals forces and/or ionic bonds and having substantially no covalent bonds between the dextran molecules. Thus, the molecules in the microparticles are preferably not intentionally cross-linked (i.e., a cross linking step is not carried out) and the microparticles contain no covalent bonds between molecules or less than 10% covalent bonds between molecules.

Figure 4:
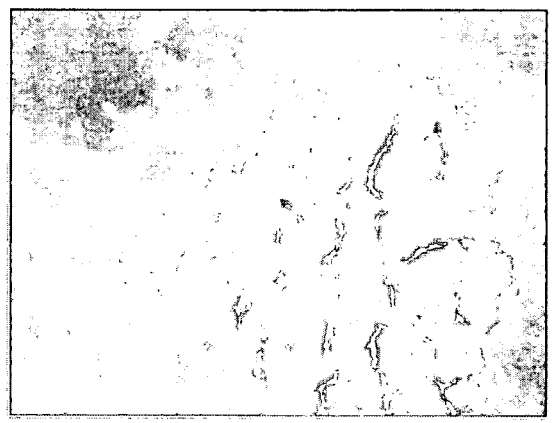
FIG. 4 is a photograph of a slow release of the fluorescently labeled macromolecules from the implant which includes crystallized dextran microparticles into mouse muscle tissue on the $14^{th}$ day after intermuscular injection.

The slow release of macromolecules from implants has been demonstrated in experiments where macromolecules were dissolved in aqueous suspensions of crystallized dextran microparticles or their aggregates before injections. FIG. 4 shows an implant containing fluorescently labeled macromolecules (FITC-dextran, MW 500 kDa) and slow release of the macromolecules from the implant into a mouse muscle tissue on the $14^{th}$ day after the intermuscular injection.

B. Two-phase System

Self assembled structures of implants based on crystallized dextran microparticles and their aggregates may be formed based on two phase systems.

Colloidal systems such as droplets of oil, liposomes, micro-and nano-particles can be dispersed in a suspension of crystallized dextran microparticles and injected to form an implant releasing therapeutic agent(s) following administration into the mammal body.

For example, in the case of oil, a special kind of implant structure can be formed where the oil core is surrounded with a shell composed of crystallized dextran microparticles or aggregates thereof dispersed in water or aqueous solutions of organic polymers such as polysaccharides (e.g. dextrans). The structure described can be designated as a capsule. It should be noted that the shell may comprise a roughly spherical shaped shell which results when the capsule is surrounded by tissue. However, when the capsule is located near a barrier, such as a substrate, bone or intestine wall, the capsule may comprise a core located between one or more walls of microparticles on one side and the barrier on the other side. Furthermore, while oil is used as an illustrative example, the core may comprise other materials, such as other polymers, cells, etc.

To form the capsule structure, two-phase aqueous systems are applied. When aqueous solutions of different polymers are mixed above certain concentrations they frequently form immiscible-liquid two-phase solutions. Each of the phases usually consists of more than 90% water and can be buffered and made isotonic. If a cell or particle suspension is added to such a system, the cells or particles are frequently found to have partitioned unequally between phases. This preferential partition behavior can be used as a basis for separation procedures for differing cell populations or particles since partition in these systems is determined directly by cell or particle surface properties. Cells or particles which do not have identical surface properties exhibit sufficiently different partition behavior.

The competitive adsorption of the two polymer phase depends on the chemical nature of the polymers. A two-phase polymer method has been applied to separate or partition cells, proteins, nucleic acids and minerals ("Partitioning in Aqueous Two-Phase Systems", 1985, eds., H. Walter, D. Brooks, and D. Fisher, pubis. Academic Press).

Figure 5:
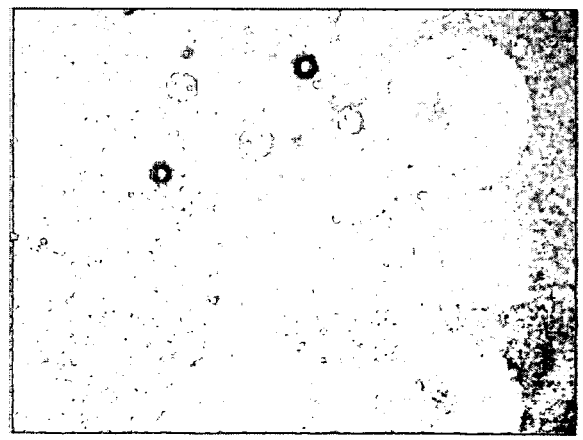
FIG. 5 is a photograph of an emulsion of aqueous solution of PEG in aqueous solution of dextran (MW 500 kDa) containing crystallized dextran microparticles shown in FIG. 1.
Figure 6:
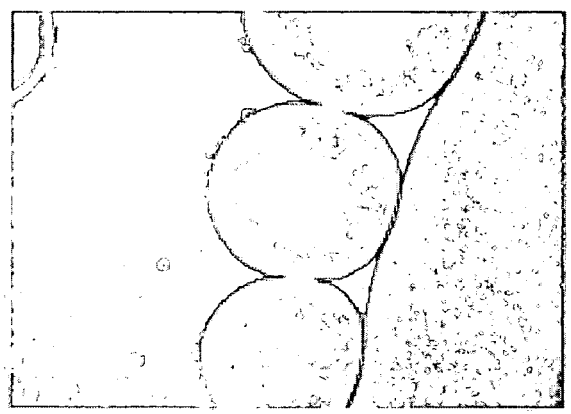
FIG. 6 is a photograph of an emulsion of aqueous solution of dextran (MW 500 kDa) containing crystallized dextran microparticles shown in FIG. 1 in aqueous solution of PEG.

The experiments with the distribution of crystallized dextran microparticles in phase systems derived from, for instance, dextran/polyethylene glycol (PEG) mixtures, revealed that the dextran microparticles prefer to be in the dextran phase, while another PEG phase can be dispersed in this dextran phase to form a W/W emulsion and vice versa in the case when the volume of the PEG phase is bigger than the volume of the dextran phase, as shown in FIGS. 5 and 6.

FIG. 5 is a photograph of an emulsion of aqueous solution of PEG in aqueous solution of dextran containing crystallized dextran microparticles. In the structure of FIG. 5, the volume of the PEG phase is less than the volume of the dextran phase. The dextran phase contains the dextran and the crystallized dextran microparticles. Thus, the PEG phase forms into one or more sphere shaped cores surrounded by dextran/dextran microparticle shells (i.e., a closed pore structure).

FIG. 6 is a photograph of an emulsion of aqueous solution of dextran containing crystallized dextran microparticles in aqueous solution of PEG, where the volume of the PEG phase is greater than the volume of the dextran phase. In this case, the dextran phase forms into one or more sphere shaped cores containing the dextran microparticles surrounded by a PEG phase (i.e., an open pore structure that is forming in vivo while PEG dissipates in tissue liquid). As can be seen in FIG. 6, the smaller volume (droplet) dextran phase forms into a large spherical dextran/dextran microparticle core (bottom right of FIG. 6) to which smaller spheres comprising dextran/dextran microparticles are joining and fuse with.

Thus, when the ratio of the volume of the first phase (such as the PEG phase and its inclusions, such as a therapeutic agent) to the volume of the second phase (such as the dextran phase and its inclusions, such as the dextran microparticles) is less than one, then the capsule forms by self assembly with a first phase core surrounded by a second phase shell. If the composition contains a therapeutic agent, such as insulin, which prefers to partition into the PEG phase, and the dextran microparticles which prefer to partition into the dextran phase, then the therapeutic agent selectively partitions into the PEG core while the microparticles selectively partition into and form the shell around the PEG core by self assembly.

The emulsion can be prepared by the mixing of separately prepared dextran and PEG phases and both can be suspensions of different types of particles that prefer to be in the PEG phase or in the dextran phase respectively. The principle is that the partition of particles into different polymer phases depends on their surface structure and interfacial energy of the particles in the polymer solutions.

Figure 7:
FIG. 7 is a photograph of an intramuscular injection of emulsion of aqueous solution of PEG in aqueous solution of dextran (MW 500 kDa) containing crystallized dextran microparticles shown in FIG. 1.
Figure 8:
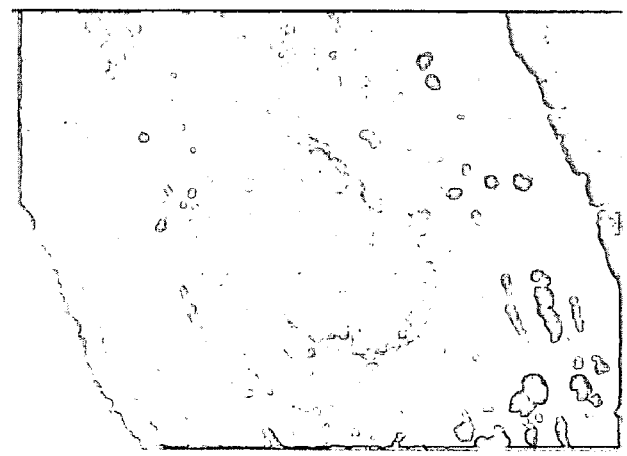
FIG. 8 is a photograph of a subcutaneous injection of emulsion of aqueous solution of PEG in aqueous solution of dextran (MW 500 kDa) containing crystallized dextran microparticles shown in FIG. 1.

Injection of aqueous two phase systems containing crystallized dextran microparticles into tissues of experimental animals revealed the formation of implants with the capsule structure as shown in FIGS. 7 and 8. The volume of the dextran phase is greater than the volume of the PEG phase in the two-phase system. Both FIGS. 7 and 8 show that a capsule with a PEG core and a dextran/dextran microparticle shell forms by self assembly in vivo (i.e., after injection into mammal tissue). The shell comprises macroporous regions between adjacent microparticles as well as microporous regions in the microparticles themselves.

A non limiting example of a method of forming a capsule structure from a two phase system is as follows. 10 g of dextran T40 (40 kDa molecular weight) and 2 g of PEG are dissolved in 88 ml of (Actrapid®) insulin solution containing 1,000 IU to which 25 g of crystallized dextran microparticles are added. These steps are performed under laminar flow conditions. The mixture is stirred on a magnetic stirrer at 100 rpm at room temperature for 30 minutes to form a homogeneous mixture (i.e., a suspension). 1.0 g of the suspension contains 8 IU of insulin.

It should be noted that the dextran microparticles may be prepared from a different molecular weight dextran solution than the dextran solution which is provided in the two phase system. Thus, the crystallized dextran microparticles may be formed in a lower molecular weight dextran solution, such as a 2 to 20 kDa solution, than the dextran solution which is provided into the two phase system, which may be a 40 to 500 kDa dextran solution, such as a 40 to 75 kDa solution. This is advantageous because the higher molecular weight dextran solutions, such as 40 and 70 kDa solutions, have received wider regulatory approval and can be used to form a shell of a capsule at lower concentrations. The lower molecular weight solutions may be used to decrease the crystallization time without the lower molecular weight dextran solution actually being provided in vivo. Furthermore, lower molecular weight microparticles may dissolve easier in vivo.

The capsule structure formed from a two phase system is advantageous because it allows for a more even and prolonged release of the therapeutic agent from the core than from a composition comprising a single phase containing the microparticles. Furthermore, it is believed that by using the capsule structure, a lower amount of microparticles may be needed to achieve the same or better timed release of a therapeutic agent than if a single phase system is used. Furthermore, by controlling the amount of microparticles in the two phase system, it is believed that the thickness of the microparticle shell may be controlled. A thicker shell results from a larger amount of microparticles in the two phase system. Thus, the amount, duration and/or timing of the release of the therapeutic agent from the capsule core may be controlled by controlling the thickness of the shell. Therefore, the release profile of the therapeutic agent may be customized for each patient or groups of patients.

Figure 9A:
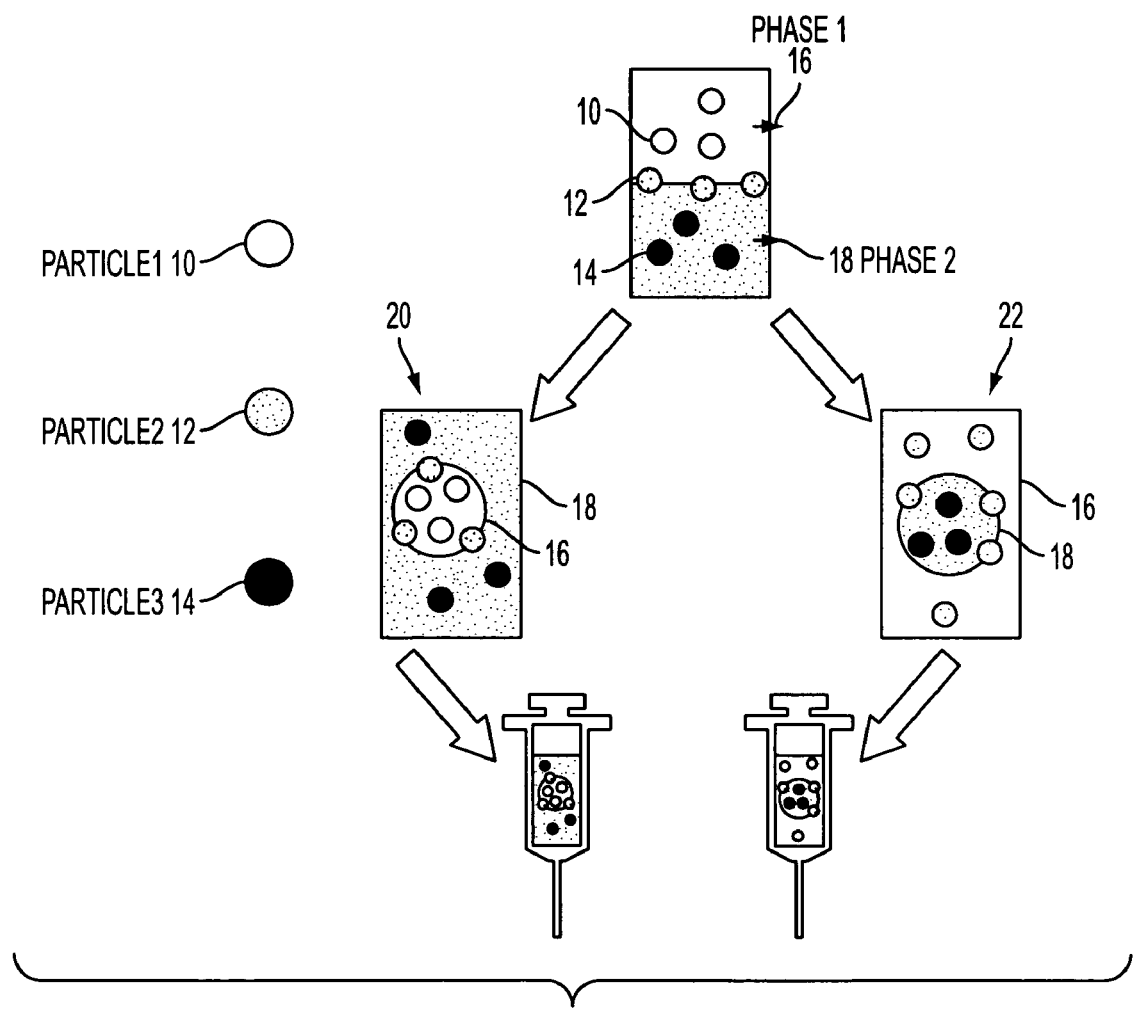
FIGS. 9A and 9C schematically illustrate partition behavior of different types of particles and phases in an aqueous two phase system.

It should be noted that while PEG and dextran are used as examples of the materials of the two phases, any other suitable materials which show the following partition behavior may be used instead. FIG. 9A schematically illustrates partition behavior of different types of particles in an aqueous two phase system. For example, three types of molecules or molecular aggregates, which are preferably particles 10, 12 and 14, and two phases 16 and 18 are shown in FIG. 9A. However, there may be two, or more than three types of particles. The particles may be microparticles such as microspheres or nanospheres prepared from organic and/or inorganic materials, liposomes, living cells, viruses and macromolecules. The first type particles 10 preferentially segregate into the first phase 16. The second type particles 12 preferentially segregate to the boundary of the first 16 and second 18 phases. The third type particles 14 preferentially segregate into the second phase 18. Thus, by analogy to the previous non-limiting example, the first particles 10 may comprise a therapeutic agent, the second 12 and/or the third 14 particles may comprise crystallized dextran microparticles, the first phase 16 may comprise a PEG phase and the second phase 18 may comprise a dextran phase.

If a smaller amount of the first phase 16 is provided into a larger amount of the second phase 18, as shown in area 20 of FIG. 9A, then a capsule type structure forms comprising discreet spheres of the first phase 16 containing a concentration of the first type particles 10, located in a second phase 18. The second type particles 12 may be located at the interface of the phases 16, 18 and act as a shell of the capsule. Particles 14 are dispersed in the second phase 18 and/or form a shell of the capsule.

In contrast, if a smaller amount of the second phase 18 is provided into a larger amount of the first phase 16, as shown in area 22 of FIG. 9A, then a capsule type structure forms comprising discreet spheres of the second phase 18 containing a concentration of the third type particles 14, located in a first phase 16. The second type particles 12 may be located at the interface of the phases 16, 18 and act as a shell of the capsule. Particles 10 are dispersed in the first phase 16 and/or form a shell of the capsule. The two phase systems 20 and 22 may be used as an implant, such as by being injected into a mammal, such as an animal or human. Thus, the capsule forms a structured, three dimensional implant, with the core acting as a reservoir or depot for controlled release of the therapeutic agent through the shell. In contrast, an implant with an even distribution of microparticles is an unstructured implant.

Furthermore, particles 10, 12 and 14 may be substituted by a liquid material (e.g. oils) or macromolecules which selectively partition into one of the phases. For example, a therapeutic agent, such as insulin, may be partitioned in PEG phase of the PEG/dextran two phase system. Since insulin selectively partitions into the PEG phase, the PEG phase forms an insulin containing core of a capsule structure. It should be noted that while certain particles and therapeutic agents selectively partition, the term "selectively partitioned" does not necessarily mean that 100 percent of the particles or therapeutic agent partition into one of the phases. However, a majority of the selectively partitioned specie, preferably 80% of the partitioned specie, partitions into one of the phases. For example, while a majority of insulin partitions into the PEG phase, a portion of insulin may remain in the dextran phase.

Figure 9B:
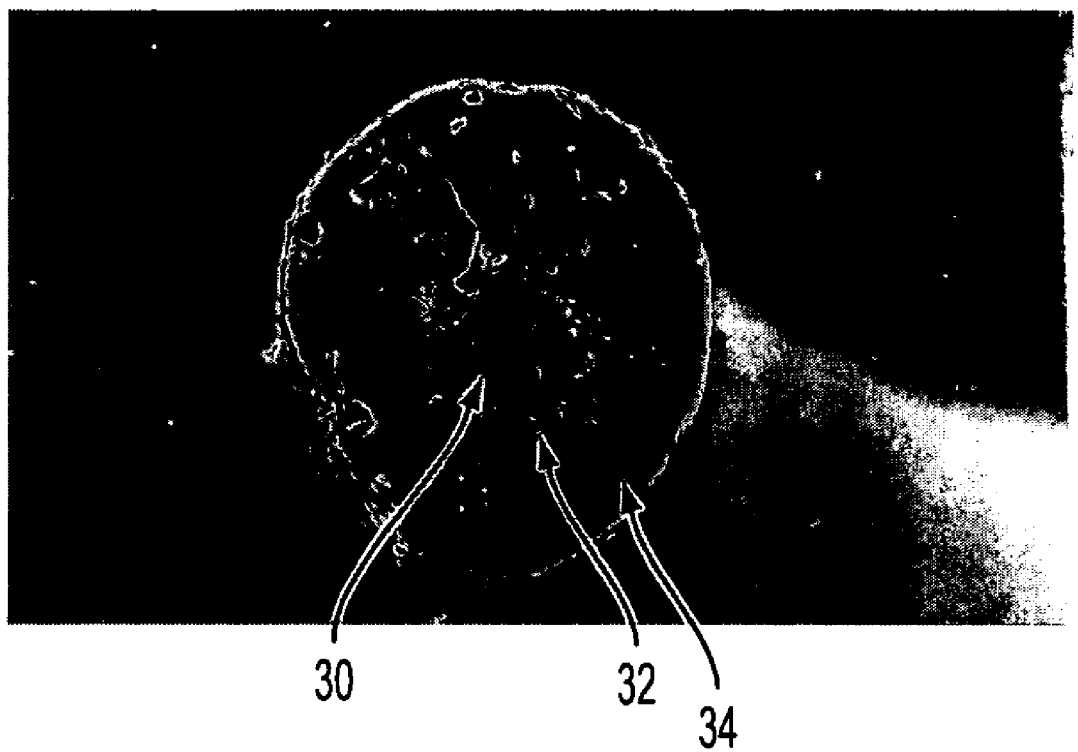
FIG. 9B is a photograph of a cross section of an implant structure based on the two phase system.

FIG. 9B illustrates a scanning electron microscope image of a cross section of an implant structure based on the two phase system schematically illustrated in FIG. 9A. A two phase aqueous composition comprising a first dextran phase, a second PEG phase and crystallized dextran microparticles was injected into sepharose gel. This gel's composition mimics mammal tissue by stopping crystallized dextran microparticles diffusion from the injection side. The image in FIG. 9B illustrates the formation of a core-shell implant structure. The core comprises regions 30 and 32 surrounded by a shell 34. Region 30 is a void that is filled with a PEG phase region prior to cutting the gel for cross sectional SEM imaging. The PEG phase region drips out of the gel when the gel is cut during cross sectioning. Region 32 is an outer portion of the core comprising PEG droplets located in the crystallized dextran microparticles. Region 34 is the shell comprising the crystallized dextran microparticles which surrounds and holds in place the PEG containing core.

Figure 9C:
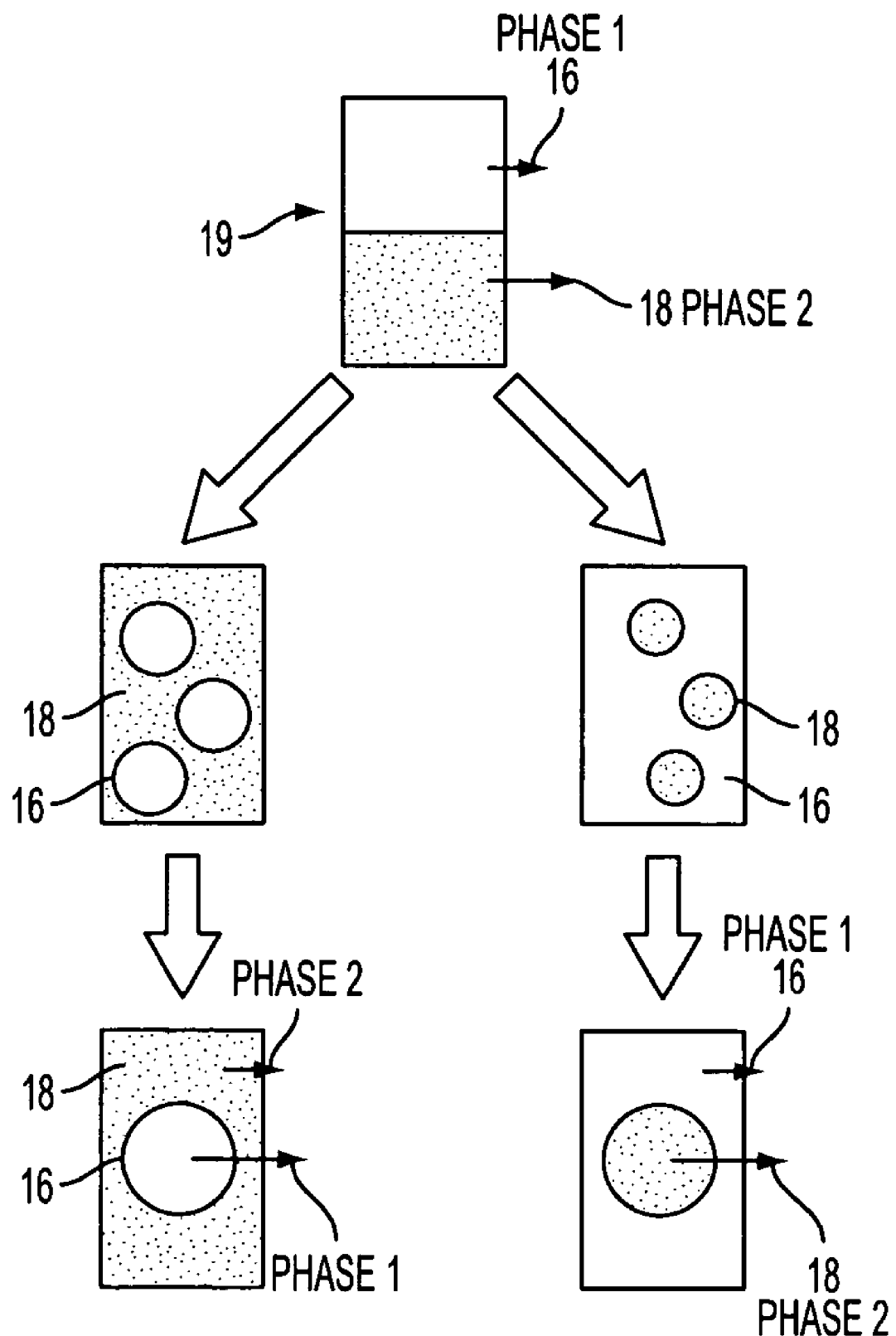

Without wishing to be bound by a particular theory, the present inventor believes that the core-shell structure shown in FIG. 9B forms by self assembly as shown schematically in FIG. 9C. While the first 16 and second 18 phases, such as aqueous solutions of different, incompatible polymers, are in a suitable storage container 19, such as in a glass beaker or vial, one phase 16 rises above the other phase 18. When the two phase composition is injected into a material which restricts free flow of the phases 16 and 18, such as mammal tissue or a substrate material, such as a gel which mimics the tissue, the composition self assembles into the core-shell structure. First, the phase that is present in the smaller volume forms into approximate spherical shapes, as shown in the middle portion of FIG. 9C. Then the spherical shapes join to form approximately spherical cores of one phase surrounded by shells of the other phase, as shown in the bottom of FIG. 9C. While a two phase system example of a multiphase system has been illustrated, the multiphase system may have more than two phases if desired.

C. Injectable Insulin Delivery Vehicle

Figure 10:
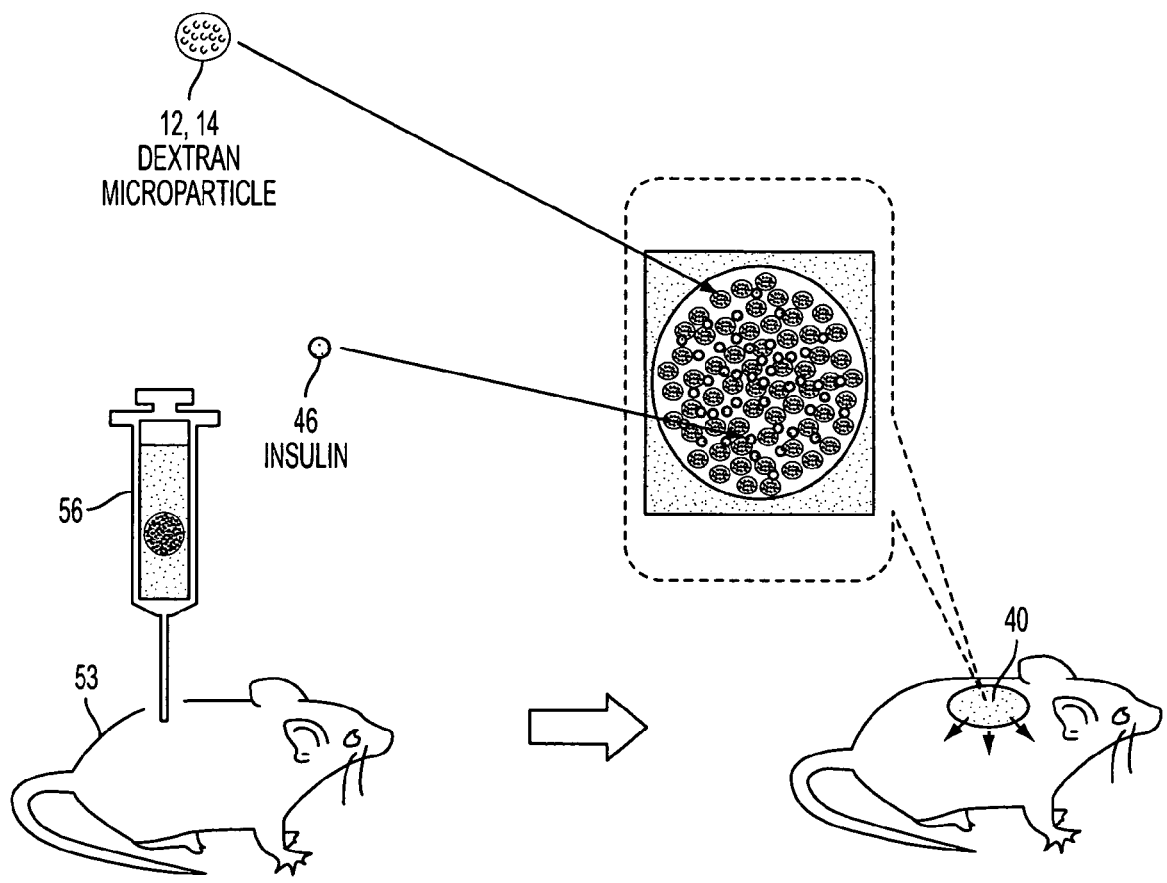
FIGS. 10 and 11 schematically illustrate therapeutic agent delivery methods according to embodiments of the present invention.
Figure 11:
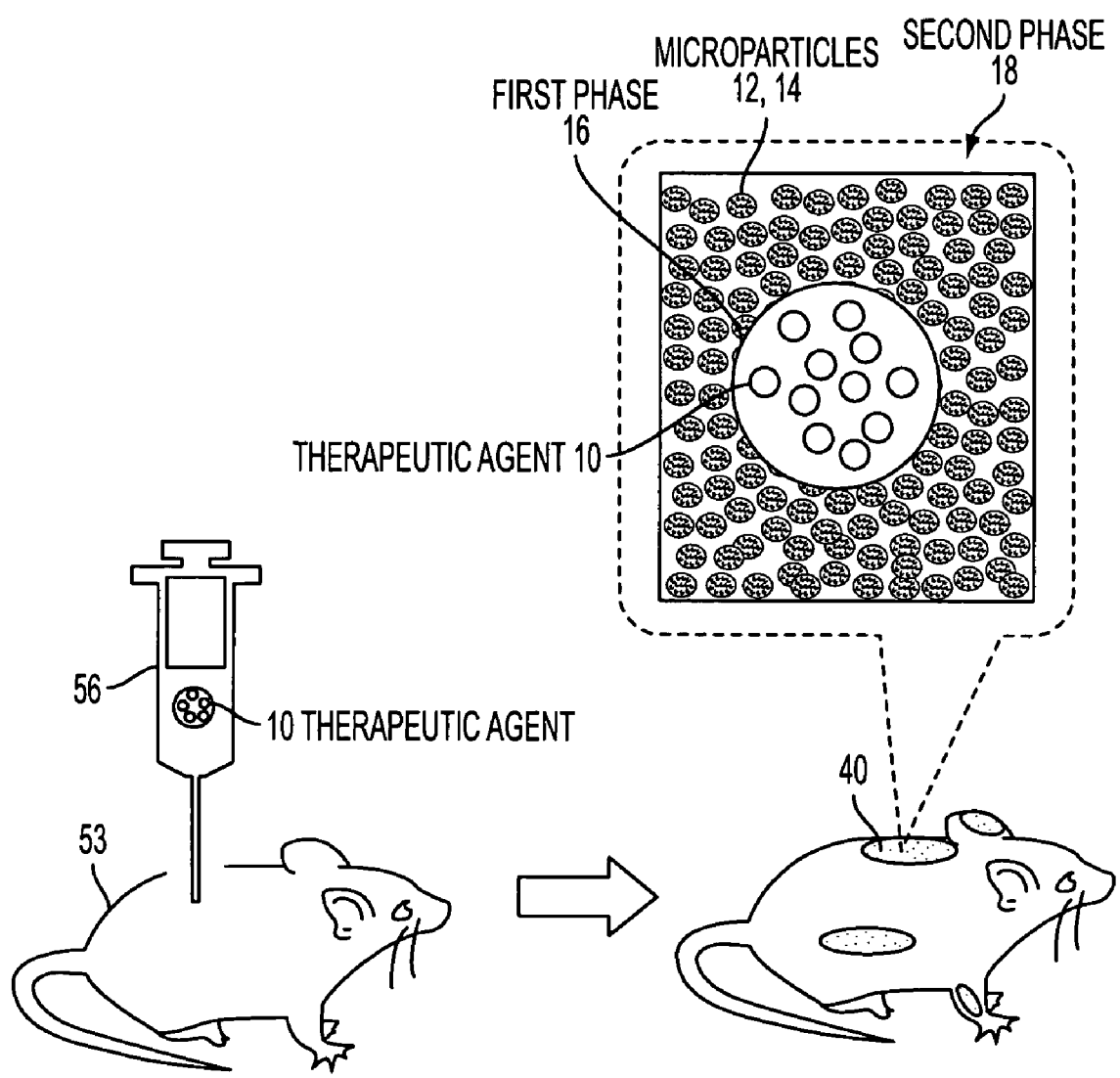

The present inventor has discovered that a composition of crystallized dextran microparticles and insulin injected into mammals, such as mice and rabbits, unexpectedly extended the duration of efficacy of the insulin compared to injections of the same dose of the same insulin alone. FIG. 10 schematically illustrates the formation of an implant 40 in a mammal 53 by injection of a one phase composition comprising the microparticles 12, 14 and insulin 46 using a syringe 56. FIG. 11 schematically illustrates the formation of a structured implant 40 in a mammal 53 by injection of a two phase composition comprising a dextran phase 18 containing selectively partitioned crystallized dextran microparticles 12, 14 and a PEG phase 16 containing selectively partitioned therapeutic agent 10 comprising insulin. The dextran phase 18 forms a shell around the PEG phase 16 core. Since mice and rabbits are a common model for humans in drug testing, the present inventor believes that the composition comprising crystallized dextran microparticles and insulin would also be effective in extending the duration of efficacy of the insulin when injected into human adults and children.

Examples 1-8 illustrate the advantage of using crystallized dextran microparticles as an injectable insulin delivery vehicle compared to injected insulin alone. The experiment involved mice and the observation was made of their response to a subcutaneously injected aqueous suspension consisting of crystallized dextran microparticles and human recombinant insulin (NovoNordisk Actrapid HM Penfill®, 40 UI/ml).

The suspension was prepared as follows. 5.0 g of Dextran T10 (Pharmacia, Uppsala, Sweden) was dissolved in 20.0 g of water. The solution was filtered through a 0.22 µm filter (Millipore, Bedford, Mass.) and freeze dried. 3.0 g of the resulting powder was dissolved in 3.0 g of sterile water and placed in box at temperature 60° C. 6 hours later, crystallized dextran microparticles were washed by centrifugation at 3,000 g with 3×5.0 ml of sterile water. Finally, the produced crystallized dextran microparticles suspension was mixed with aqueous insulin solution and used in the experiment with mice. Samples of the suspension were introduced into the mice's legs and samples of animal blood were taken from each mouse's tail and analyzed for glucose concentrations. Blood glucose was measured using the glucose oxidase method on a One-touch system glucose analyzer (Lifescan, Johnson & Johnson, Milpitas, Calif., USA) after proper calibration.

In comparative example 1, no insulin was injected into the mouse. In comparative examples 2, 3 and 7, insulin alone (0.5 UI) was injected into the three mice. In examples 4-6 and 8, insulin (0.5 UI) and a crystallized dextran microparticles implant was injected into the four mice. The results are summarized in Table I.

TABLE I

| Ex # | | 0 min glucose mmol/l | 15 min glucose mmol/l | 30 min glucose mmol/l | 45 min glucose mmol/l | 120 min glucose mmol/l | 210 min glucose mmol/l | 270 min glucose mmol/l | 390 min glucose mmol/l |
|---|---|---|---|---|---|---|---|---|---|
| 1 | Intact mouse | 7.9 | 8.1 | 8.2 | 8.4 | — | — | — | — |
| 2 | Insulin 0.5 UI | 5.9 | 3.3 | 2.7 | 1.8 | 0.9 | 3.5 | 3.0 | 3.2 |
| 3 | Insulin 0.5 UI | 8.1 | 3.8 | 2.8 | 1.9 | 0.9 | 3.7 | 3.4 | 3.5 |
| 4 | Insulin 0.5 UI with crystallized dextran microparticles | 6.0 | 4.3 | 3.2 | 2.5 | 0.8 | 0.8 | 0.9 | 0.7 |

TABLE I-continued

| Ex # | | 0 min glucose mmol/l | 15 min glucose mmol/l | 30 min glucose mmol/l | 45 min glucose mmol/l | 120 min glucose mmol/l | 210 min glucose mmol/l | 270 min glucose mmol/l | 390 min glucose mmol/l |
|---|---|---|---|---|---|---|---|---|---|
| 5 | Insulin 0.5 UI with crystallized dextran microparticles | 6.9 | 5.6 | 4.1 | 3.4 | — | 1.2 | — | 1.6 |
| 6 | Insulin 0.5 UI with crystallized dextran microparticles | 5.9 | 3.5 | 2.9 | 1.9 | 1.2 | 1.0 | 1.0 | 0.7 |
| 7 | Insulin 0.5 UI (average) | 7 | 3.6 | 2.8 | 1.9 | 0.9 | 3.6 | 3.2 | 3.4 |
| 8 | Insulin 0.5 UI with crystallized dextran microparticles (average) | 6.3 | 4.5 | 3.4 | 2.6 | 1.0 | 1.0 | 1.0 | 1.0 |

The average reduction of sugar in the blood (i.e., blood glucose) of animals is very different when 0.5 UI i.m. were applied with and without crystallized dextran microparticles. As shown in Table I, the glucose level in the mice of comparative examples 2, 3 and 7 is about the same or lower than the glucose level in mice of examples 4-6 and 8 during the first 45 minutes after injection. The glucose level is about the same in mice of both comparative examples 2, 3 and 7 and examples 4-6 and 8, 120 minutes after injection. However, the glucose level in the mice of comparative examples 2, 3 and 7 is about three times higher than the glucose level in mice of examples 4-6 and 8 from 210 to 390 minutes after injection. In fact, the blood glucose level in mice in examples 4-6 and 8 did not substantially increase (i.e., did not increase by more than 10%, remained the same or decreased) from 120 minutes to 390 minutes after injection. In contrast, the blood glucose level in mice in the comparative examples 2, 3 and 7 injected with the same amount of insulin did substantially increase from 120 to 390 minutes after injection. The crystallized dextran microparticles/insulin injection decreases blood glucose for a longer time than an injection of insulin of the same dose alone. Thus, the composition containing crystallized dextran microparticles and insulin may be dosed for injection.

The following experiments on rabbits also demonstrate how the crystallized dextran microparticles/insulin injection decreases blood glucose and maintains a basal level of blood insulin for a longer time than an injection of the same insulin of the same dose alone. A subcutaneously injected composition comprising Actrapid HM® short-acting insulin and crystallized dextran microparticles was unexpectedly found to extend the duration of efficacy of this short-acting insulin to exceed that of subcutaneously injected, long-acting insulin Monotard HM® alone.

The term duration of efficacy means decreasing blood glucose concentration and/or maintaining a basal level of blood insulin concentration to desired levels independent of external events that cause spikes in blood glucose, such as eating. Thus, the term duration of efficacy is a relative term comparing the efficacy of the insulin and microparticle composition to that of the same dose of the same insulin alone. In other words, the duration of efficacy is a duration of action or a duration of pharmacological effect, which may be measured in a patient in a fasting state to compare the efficacy of the insulin and microparticle composition to that of the same dose of the same insulin alone.

Figure 12A:
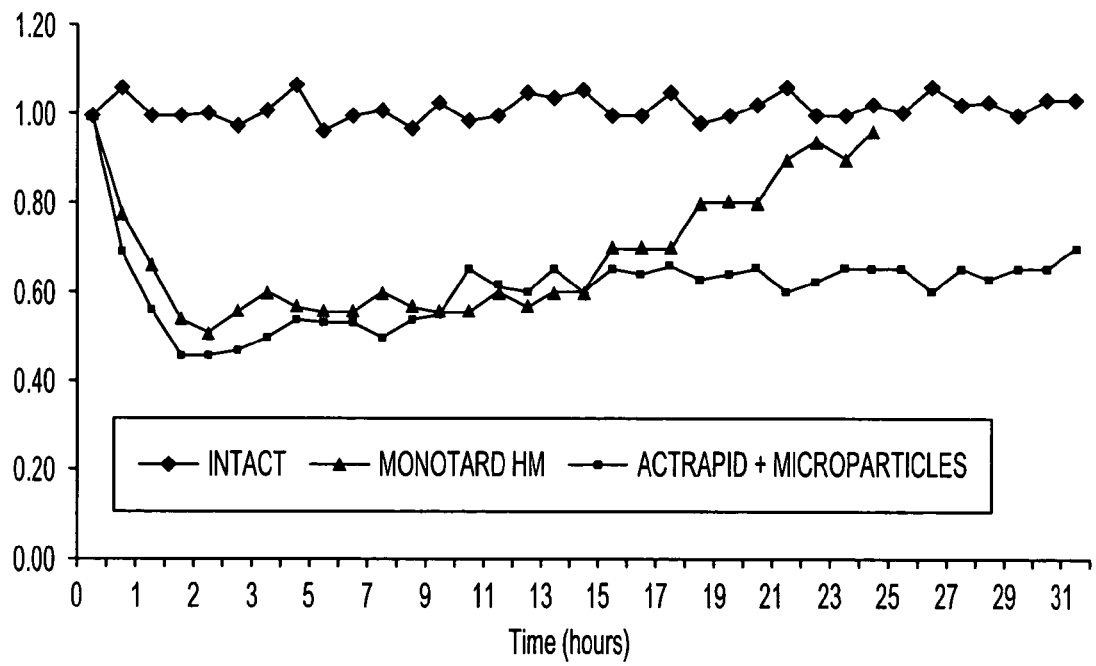
FIGS. 12A and 12B are graphs of relative normalized of blood glucose concentrations for various insulin containing composition versus time.
Figure 12B:
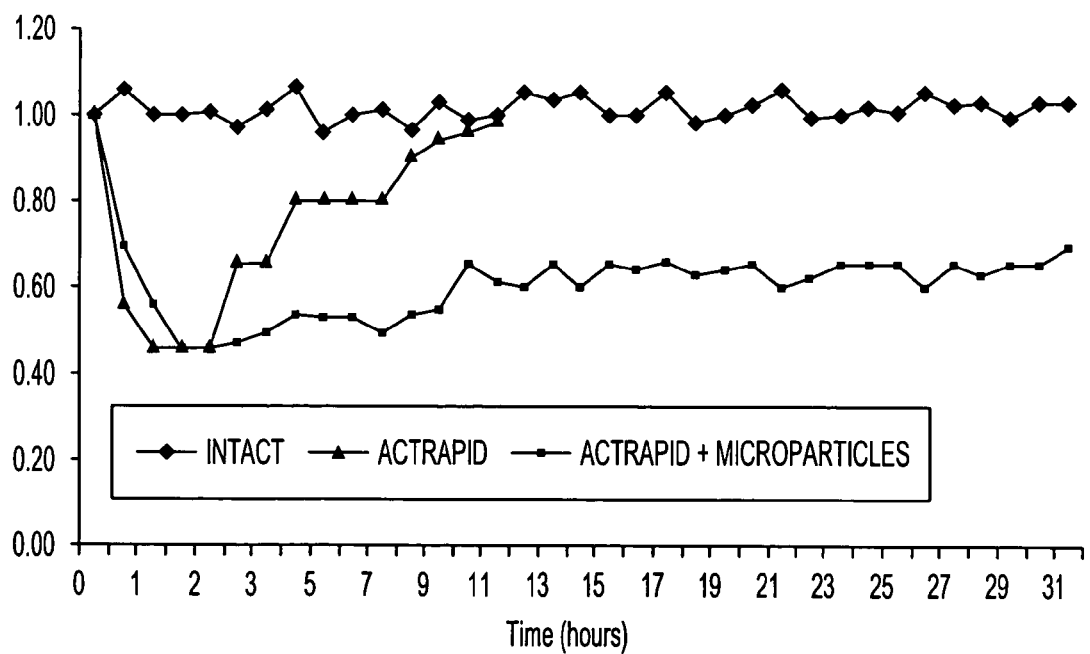

As shown in FIGS. 12A and 12B, the composition comprising the Actrapid HM® short-acting insulin and crystallized dextran microparticles prolonged the absorption of insulin and extended the hypoglycemic effect (i.e., the duration of efficacy of the insulin) to at least twenty four hours, such as about twenty eight to about thirty one hours, as compared to about two to about eight hours for Actrapid HM® insulin alone (FIG. 12B) and about seventeen to about twenty-four hours for long-acting "Monotard HM"® insulin alone (FIG. 12A). Both Actrapid HM® and Monotard HM® insulins are products of Novo Nordisk and the advertised duration of efficacy of these insulin compositions in humans obtained from company information are eight and twenty four hours, respectively.

In FIGS. 12A and 12B, the upper line illustrates the control line for intact rabbits to which no insulin was administered. The y-axis of FIGS. 12A and 12B is a relative normalized scale of blood glucose concentration for the same 8 IU dose of insulin. The data in the Figures was adjusted to be shown in one plot for each figure and shows blood glucose levels in blood of animals following insulin injections.

The data shown in FIGS. 12A and 12B was obtained as follows. Chinchilla rabbits (2.3±0.3 kg) were monitored for their response to injections of a formulation consisting of crystallized dextran microparticles and short-acting insulin Actrapid HM®. Samples of the formulation were subcutaneously injected into the rabbits. Long acting insulin Monotard HM® (40 IU/ml) and short acting insulin Actrapid HM® were subcutaneously injected into separate rabbits without the microparticles and used as controls. Samples of animal blood were taken from the rabbit's ear vein and analyzed for glucose concentration. Blood glucose concentration was measured with a glucose analyzer (One-Touch® Lifescan, Johnson & Johnson, Milpitas, Calif., USA) after proper calibration.

In comparative examples 9 and 10, two intact rabbits were not provided any insulin. In comparative examples 11 and 12 an aqueous solution of long-acting insulin Monotard HM® was introduced subcutaneously to two rabbits in a dose of 8 IU. In examples 13-15, a suspension of crystallized dextran microparticles with short-acting insulin Actrapid HM® was introduced subcutaneously to three rabbits in a dose of 8 IU. The results of the experiments are summarized in Table II.

because it extends the efficacy without increasing the amount of insulin. Current prior art long-acting diabetes therapies are

TABLE II

| Ex # | Insulin dose | 0 hours glucose mmol/L | 0.5 hours glucose mmol/L | 1 hour glucose mmol/L | 1.5 hours glucose mmol/L | 2 hours glucose mmol/L | 2.5 hours glucose mmol/L | 16 hours glucose mmol/L | 24 hours glucose mmol/L | 31 hours glucose mmol/L |
|---|---|---|---|---|---|---|---|---|---|---|
| 9  | 0.0  | 5.4 | 5.0 | 5.2 | 5.2 | 5.2 | 5.4 | 4.7 | 5.4 | 5.4 |
| 10 | 0.0  | 6.0 | 6.3 | 6.3 | 6.3 | 6.3 | 6.4 | 5.7 | 5.6 | 5.8 |
| 11 | 8 IU | 5.4 | 5.8 | 3.8 | 3.2 | 2.4 | 2.6 | 3.9 | 5.6 | N.A |
| 12 | 8 IU | 5.4 | 5.0 | 4.2 | 2.9 | 2.5 | 2.4 | 4.0 | 5.1 | N.A |
| 13 | 8 IU | 5.8 | 3.7 | 1.9 | 1.9 | 1.9 | 2.8 | 4.1 | 4.3 | 4.1 |
| 14 | 8 IU | 6.6 | 5.7 | 4.3 | 3.9 | 3.7 | 3.9 | 4.6 | 4.1 | 3.9 |
| 15 | 8 IU | 6.2 | 5.1 | 3.6 | 3.2 | 3.1 | 2.9 | 4.2 | 4.4 | 4.7 |

The above examples 13-15 illustrate that the composition of crystallized dextran microparticles with short-acting insulin Actrapid HM® provides a prolonged effect that exceeds the effect of long acting insulin Monotard HM® and is believed to be comparable to the effect of long acting (once daily dosing) insulin glargine Lantus® from Aventis (see www.aventis-us.com/Pls/lantus_TXT.html). In addition, Lantus® insulin must not be diluted or mixed with any other insulin or solution. If Lantus® insulin is diluted or mixed, the pharmacokinetic/pharmacodynamic profile (e.g., onset of action, time to peak effect) of Lantus® and/or the mixed insulin may be altered in an unpredictable manner. In contrast, the composition of crystallized dextran microparticles with insulin is not so limited because any suitable insulin, such as human insulin, may be used. In the composition of crystallized dextran microparticles and insulin, the ratio of insulin and microparticles can be varied as desired. Furthermore, any suitable insulin may be used to custom fit an insulin therapy to an individual patient. Thus, Actrapid HM® was used in the composition as an illustrative example of a typical insulin and the composition is not limited to this brand of insulin.

As shown in examples 9-15, the composition containing the crystallized dextran microparticles and insulin is effective in maintaining a duration of efficacy of the insulin for at least 30% longer, such as at least 100% longer, preferably 100 to 400% longer than the same dose of the same insulin without the microparticles. The microparticle containing insulin composition is effective in maintaining a desired basal level of blood insulin and blood glucose concentration for at least 30% longer, such as 100% to 400% longer, than the same dose of the same insulin without the microparticles. Thus, the duration of efficacy of the microparticle containing composition is at least 24 hours, which allows it to be injected only once daily into the mammal, such as a human in need thereof.

The long lasting insulin crystallized dextran microparticle composition is safer than prior art long lasting insulin compositions because it can achieve the long lasting efficacy without using a higher dose of insulin as in the prior art compositions. For example, if a 8 IU dose of short acting insulin has been determined medically safe for a patient without a significant risk of overdose, then the composition comprising the same short acting insulin and the crystallized dextran microparticles can provide longer acting duration efficacy at the same 8 IU dose of short acting insulin without a significant risk of overdose, even if all the insulin is released into the patient at once. Furthermore, this composition provides a cost saving compared to the prior art compositions made with analogs of insulin, such as the Lantus® insulin from Aventis. In contrast, the crystallized dextran microparticle containing composition preferably contains human recombinant insulin whose safety profile is established. Thus, this composition reduces the risk of adverse reaction(s) and number of injections to diabetics, thereby enhancing the quality of life of the diabetics.

The injectable composition may comprise a single phase system comprising insulin and microparticles or a two phase system which forms a PEG and insulin core and a dextran and dextran microparticle shell for an even greater duration of efficacy. Furthermore, the composition comprises a flowable one phase or multiphase colloidal system (i.e., a suspension or an emulsion) which is relatively easy to inject into a mammal.

The following example illustrates the use of an injectable two phase composition comprising a dextran phase, a PEG phase, insulin and crystallized dextran microparticles. It is believed that when injected into a mammal, this composition forms a structured reservoir type implant having a three dimensional capsule structure. In the capsule structure, the microparticles selectively partition into the dextran phase and the insulin selectively partitions into the PEG phase. The dextran phase containing the microparticles forms a shell around a core comprising the PEG phase containing the insulin. This structured implant allows for controlled release from the core through the shell.

In comparative example 16, 0.5 IU of Actrapid HM® insulin (100 IU/ml) is subcutaneously injected into a mouse. In example 17, 0.4 g of crystallized dextran microparticles are dispersed in 0.6 ml of 20% (W/W) aqueous solution of dextran having a molecular weight of 70 kDa (Pharmacia, Sweden) to form a suspension. 10 mg of PEG having a molecular weight 6 kDa (Fluka) is dissolved in 0.1 ml of Actrapid HM® insulin (100 IU/ml) to form a solution. 0.05 ml of the PEG and insulin solution is mixed with 0.15 ml of the microparticle and dextran suspension to form a two phase composition or mixture. 0.02 ml of the two phase mixture containing 0.5 IU of insulin is injected subcutaneously into mouse. The results are shown in Table III.

TABLE III

| Example # | 0 min glucose mmol/L | 15 min glucose mmol/L | 30 min glucose mmol/L | 45 min glucose mmol/L | 60 min glucose mmol/L | 120 min glucose mmol/L |
|---|---|---|---|---|---|---|
| 16 | 7.8 | 3.7 | 2.3 | 1.7 | 2.9 | 6.7 |
| 17 | 7.9 | 5.9 | 4.3 | 4.1 | 4.3 | 4.0 |

As can be seen in Table III, the two phase composition duration of efficacy was longer than that of the insulin alone. Furthermore, the two phase composition decreased the blood glucose concentration more gradually than insulin alone. Without wishing to be bound by a particular theory, these effects are believed due to the controlled insulin release from the core of capsule structure.

Furthermore, the microparticle containing composition may be individually tailored for each patient by adjusting the amount of insulin and/or microparticles to allow the patient to inject the composition at the same time every day (i.e., once every 24 hours, once every 48 hours, etcetera). Thus, the duration of efficacy of the composition is adjustable for each patient. For a two phase system, the insulin release profile from the core of the capsule may be adjusted by controlling the amount of microparticles to control the shell thickness of the capsule.

While the inventor does not wish to, be bound by any particular theory, it is believed that the long lasting effect of the same dose of insulin in mice and rabbits with crystallized dextran microparticles can be explained by the diffusion of the insulin molecules from the crystallized dextran microparticles based implant (i.e., a self controlled release of insulin). Since mice and rabbits are a common model for humans in drug testing, the data shown in the above tables I to III suggests that the use of crystallized dextran microparticles based implants makes it possible to develop controlled release delivery systems with improved pharmacokinetic and dynamics characteristics and that better meet the needs of basal insulin patients, such as humans.

D. Materials

In the preferred embodiments of the present invention, the therapeutic agent comprises insulin. In other words, the therapeutic agent may consist essentially of insulin alone or comprise insulin in combination with another agent. The term "insulin" shall be interpreted to encompass insulin analogs, natural extracted human insulin, recombinant produced human insulin, insulin extracted from bovine and/or porcine sources, recombinant produced porcine and bovine insulin and mixtures of any of these insulin products. The term is intended to encompass the polypeptide normally used in the treatment of diabetics in a substantially purified form but encompasses the use of the term in its commercially available pharmaceutical form, which includes additional excipients. The insulin is preferably recombinant produced and may be dehydrated (completely dried) or in solution.

The terms "insulin analog," "monomeric insulin" and the like are used interchangeably herein and are intended to encompass any form of "insulin" as defined above, wherein one or more of the amino acids within the polypeptide chain has been replaced with an alternative amino acid and/or wherein one or more of the amino acids has been deleted or wherein one or more additional amino acids has been added to the polypeptide chain or amino acid sequences, which act as insulin in decreasing blood glucose levels. In general, the term "insulin analogs" of the preferred embodiments of the present invention include "insulin lispro analogs," as disclosed in U.S. Pat. No. 5,547,929, incorporated hereinto by reference in its entirety; insulin analogs including LysPro insulin and humalog insulin, and other "super insulin analogs", wherein the ability of the insulin analog to affect serum glucose levels is substantially enhanced as compared with conventional insulin as well as hepatoselective insulin analogs which are more active in the liver than in adipose tissue. Preferred analogs are monomeric insulin analogs, which are insulin-like compounds used for the same general purpose as insulin, such as insulin lispro, i.e., compounds which are administered to reduce blood glucose levels.

The term "analog" refers to a molecule, which shares a common functional activity with the molecule to which it is deemed to be comparable and typically shares common structural features as well.

The term "recombinant" refers to any type of cloned therapeutic expressed in prokaryotic cells or a genetically engineered molecule, or combinatorial library of molecules which may be further processed into another state to form a second combinatorial library, especially molecules that contain protecting groups which enhance the physicochemical, pharmacological, and clinical safety of the therapeutic agent.

The term dextran microparticles includes unsubstituted dextran microparticles and substituted dextran microparticles. For example, substituted dextran microparticles include dextran substituted with a suitable group, such as a methyl group, up to a degree which does not hamper crystallization of the dextran microparticles, such as up to 3.5 or less percent branching. The average microparticle diameter is preferably about 0.5 to about 5 microns, more preferably about 1 to about 2 microns.

Furthermore, while porous non cross-linked dextran microparticles, such as crystallized microparticles, are preferably used with the therapeutic agent, other suitable organic or inorganic microparticles may be used instead, such as other polymer microparticles including polysaccharides, PLA, PLGA, PMMA, polyimides, polyesters, acrylates, acrylamides, vinyl acetate or other polymeric materials, biomaterial particles such as alginate and cells, or inorganic particles, such as silica, glass or calcium phosphates. Preferably the microparticles are biodegradable. Preferably, porous microparticles are used. Most preferably, the microparticles have sufficient porosity to contain the therapeutic agent within the pores and to provide a timed release of the therapeutic agent from the pores. In other words, the therapeutic agent is released over time from the pores, such as in over 5 minutes, preferably in over 30 minutes, most preferably in over one hour, such as in several hours to several days, rather than all at once. Thus, the particle material, pore size and pore volume can be selected based on the type of therapeutic agent used, the volume of therapeutic agent needed for delivery, the duration of the delivery of the therapeutic agent, the environment where the therapeutic agent will be delivered and other factors.

Thus, in a preferred aspect of the present invention, the therapeutic agent is located at least partially in the pores of the porous microparticles. Preferably, the therapeutic agent is not encapsulated in the microparticle (i.e., the microparticle does not act as a shell with a therapeutic agent core inside the shell) and is not attached to the surface of the microparticle. However, if desired, a portion of the therapeutic agent may also be encapsulated in a microparticle shell and/or is attached to the surface of the microparticle in addition to being located in the pores of the microparticle. The location of the therapeutic agent in the pores provides an optimum timed release of the therapeutic agent. In contrast, the therapeutic agent attached to the surface of the microparticle is often released too quickly, while the therapeutic agent encapsulated in the microparticle is often not released soon enough and is then released all at once as the microparticle shell disintegrates. In a two phase system, at least 80% of the therapeutic agent is preferably located in a core surrounded by a wall or shell comprising the microparticles.

E. Methods of Making

The microparticles may be formed by any suitable method. Preferably, the microparticles are combined with the therapeutic agent after the microparticles are formed. Thus, the microparticles, such as the crystallized dextran microparticles are formed by any suitable method and then the therapeutic agent and the microparticles are combined by any suitable method. In contrast, in some prior art methods, the therapeutic agent is encapsulated into a microparticle shell by providing the particle precursor material and the therapeutic agent into a solution and then crystallizing or cross-linking the precursor material, such as a monomer or oligomer material, to encapsulate a therapeutic agent core into a microparticle shell.

Preferably, the therapeutic agent is provided into the pores of the porous microparticles after the microparticles are formed. Thus, the porous microparticles are first formed and then the therapeutic agent is provided into a solution containing the microparticles to allow the therapeutic agent to permeate into the pores of the microparticles. Of course, some of the therapeutic agent may also become attached to the surface of the microparticle in this process.

Thus, a method to manufacture non cross-linked, porous crystallized dextran microparticles includes preparation of a dextran solution, such as an aqueous dextran solution, conducting a crystallization process to form crystallized porous dextran microparticles, and if desired, isolating crystallized porous dextran microparticles from the solution. A therapeutic agent is then permeated into the pores of the microparticles by providing the therapeutic agent into the crystallization solution containing the microparticles or by providing the isolated microparticles and the therapeutic agent into a second solution, such as a second aqueous solution. For example, crystallized dextran microparticles may be formed in a first, low molecular weight dextran aqueous solution, such as a 2 to 20 kDa dextran solution. The microparticles are then removed from the first solution and then placed into a second dextran aqueous solution having a higher molecular weight dextran, such as a 40 to 500 kDa solution, for example, a 40 to 75 kDa solution. The second solution may comprise a first phase of a two phase system, which is then combined with a second phase, such as a PEG phase containing a therapeutic agent. A similar method may be used with other porous microparticles, where a therapeutic agent is then permeated into the pores of the microparticles after the porous microparticles are formed by any suitable microparticle formation method, including, but not limited to crystallization. The components of the composition such as insulin, microparticles and one or more aqueous phases may be combined in any suitable order sequentially or simultaneously.

Preferably, the microparticles are formed by self assembly from a solution that does not contain organic solvents and organic reaction promoters which leave an organic residue in the microparticles. Thus, for example, the dextran microparticles are preferably formed by self assembly from an aqueous dextran solution. However, if desired, organic solvents and/or organic reaction promoters may also be used. In this case, the microparticles may be purified prior to subsequent use to remove the harmful organic residue.

As described above, the capsule structure having a first phase core and a second phase wall or shell may be formed in vivo or in vitro from a two phase composition. The composition may be dried powder, such as freeze dried and stored as a powder or porous cake. When the composition is ready to be administered to a mammal, it is hydrated and administered to a mammal by injection.

Preferably, the composition which includes the microparticles and the therapeutic agent is a flowable colloidal system when the composition is dosed for injection. Examples of flowable colloidal systems include emulsions and suspensions which may be injected into a mammal using a common gage syringe or needle without undue difficulty. In contrast, some prior art compositions include a therapeutic agent in a dextran hydrogel or in a cross-linked dextran matrix. A dextran hydrogel and a cross-linked dextran matrix are not flowable compositions if not specifically prepared.

In another preferred aspect of the present invention, the microparticles comprise microparticles which are adhesive to mammalian mucosa. Preferably the adhesive microparticles are porous microparticles described above. This further improves the effective delivery of the therapeutic agent.

In another preferred aspect of the present invention, the microparticles comprise microparticles whose surface has been specially modified to enhance the adhesion of the therapeutic agent to the microparticle surface and to optimize the delivery of the therapeutic agent. The microparticle surface may contain any suitable modification that would increase the adhesion of the therapeutic agent.

The foregoing description of the invention has been presented for purposes of illustration and description. It is not intended to be exhaustive or to limit the invention to the precise form disclosed, and modifications and variations are possible in light of the above teachings or may be acquired from practice of the invention. The drawings and description were chosen in order to explain the principles of the invention and its practical application. It is intended that the scope of the invention be defined by the claims appended hereto, and their equivalents.

All of the publications and patent applications and patents cited in this specification are herein incorporated in their entirety by reference.

I claim:

1. A method of making a pharmaceutical composition suitable for injection into the body of a mammal, said method comprising:
   providing crystallized dextran microparticles that do not include insulin; and
   combining the crystallized dextran microparticles with insulin in an amount effective to lower the blood glucose level of said mammal.

2. The method of claim 1, wherein:
   the composition comprises a flowable colloidal composition; and
   the microparticles comprise crystallized dextran microparticles having an average diameter of 0.5 to 5 microns.

3. The method of claim 2, wherein:
   the composition comprises a two phase composition comprising a dextran phase and a PEG phase;
   the insulin is selectively partitioned in the PEG phase and the microparticles are selectively partitioned in the dextran phase; and
   the composition forms a structured implant comprising a PEG phase core and a dextran phase shell after injection into the body of the mammal.

4. The method of claim 1, wherein the provided crystallized dextran microparticles are porous.

5. The method of claim 4, wherein the provided crystallized dextran microparticles have a porosity of at least 10% by volume.

6. The method of claim 4, wherein the porous crystallized dextran microparticles are combined with the insulin such that at least a portion of the insulin is contained within the pores of the crystallized dextran microparticles.

7. The method of claim 1, wherein the composition is prepared to be in the form of an aqueous suspension.

8. The method of claim 1, wherein the crystallized dextran microparticles are provided in the crystallized microparticle form prior to said combining step.

9. The method of claim 1, wherein the crystallized dextran microparticles are provided in a solution comprising the formed crystallized dextran microparticles and a suitable carrier.

10. The method of claim 9, wherein said combining step comprises adding the insulin to the solution and allowing the insulin to permeate into pores present in the dextran microparticles or become attached to a surface of the dextran microparticles.

* * * * *